United States Patent
Wang et al.

(10) Patent No.: US 10,492,872 B2
(45) Date of Patent: Dec. 3, 2019

(54) SURGICAL NAVIGATION SYSTEM, SURGICAL NAVIGATION METHOD AND PROGRAM

(71) Applicant: THE UNIVERSITY OF TOKYO, Tokyo (JP)

(72) Inventors: Junchen Wang, Tokyo (JP); Hideyuki Suenaga, Tokyo (JP); Ichiro Sakuma, Tokyo (JP); Etsuko Kobayashi, Tokyo (JP); Kazuto Hoshi, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 15/765,303

(22) PCT Filed: Sep. 23, 2016

(86) PCT No.: PCT/JP2016/077979
§ 371 (c)(1),
(2) Date: Apr. 2, 2018

(87) PCT Pub. No.: WO2017/057175
PCT Pub. Date: Apr. 6, 2017

(65) Prior Publication Data
US 2018/0280091 A1  Oct. 4, 2018

(30) Foreign Application Priority Data
Oct. 2, 2015 (JP) .................................. 2015-196791

(51) Int. Cl.
*A61B 34/20* (2016.01)
*A61C 19/04* (2006.01)
(Continued)

(52) U.S. Cl.
CPC .............. *A61B 34/20* (2016.02); *A61B 34/10* (2016.02); *A61B 90/37* (2016.02); *A61C 19/04* (2013.01);
(Continued)

(58) Field of Classification Search
CPC .. H04N 13/332; H04N 5/23232; A61B 34/20; A61B 34/10; A61B 90/37
See application file for complete search history.

(56) References Cited

U.S. PATENT DOCUMENTS

| 2011/0102549 A1 | 5/2011 | Takahashi |
| 2016/0067007 A1* | 3/2016 | Piron ................... A61B 5/7246 705/3 |

FOREIGN PATENT DOCUMENTS

| JP | 2004-062671 A | 2/2004 |
| JP | 2010-259497 A | 11/2010 |
| WO | 2009/116663 A1 | 9/2009 |

OTHER PUBLICATIONS

Dec. 6, 2016 International Search Report issued in International Patent Application No. PCT/JP2016/077979.
(Continued)

*Primary Examiner* — Mishawn N. Hunter
(74) *Attorney, Agent, or Firm* — Oliff PLC

(57) ABSTRACT

A system stores clustering information obtained by clustering multiple sets of viewpoints relative to teeth of a three-dimensional model of a patient and projection images of a head including the teeth from the respective viewpoints. At the time of a surgery, the system creates comparative images from a photographed image taken by a monocular camera and searches for any viewpoint having a projection image similar to the comparative image sequentially from a first hierarchy to a final hierarchy in the clustering information. The system sets a representative viewpoint based on the viewpoint of the final hierarchy, restores position and pos-
(Continued)

ture of the teeth of the patient relative to the monocular camera as position and posture of the teeth of the three-dimensional model relative to the representative viewpoint, and generates and outputs a navigation image based on position and posture of surgical information relative to the teeth after the restoration.

8 Claims, 9 Drawing Sheets

(51) Int. Cl.
| | |
|---|---|
| A61B 34/10 | (2016.01) |
| H04N 13/332 | (2018.01) |
| H04N 5/232 | (2006.01) |
| A61B 90/00 | (2016.01) |
| A61C 1/08 | (2006.01) |
| A61B 90/50 | (2016.01) |

(52) U.S. Cl.
CPC ....... *H04N 5/23232* (2013.01); *H04N 13/332* (2018.05); *A61B 90/361* (2016.02); *A61B 2034/105* (2016.02); *A61B 2034/2057* (2016.02); *A61B 2090/366* (2016.02); *A61B 2090/372* (2016.02); *A61B 2090/502* (2016.02); *A61C 1/084* (2013.01)

(56) References Cited

OTHER PUBLICATIONS

Junchen Wang et al. "Augmented Reality Navigation With Automatic Marker-Free Image Registration Using 3-D Image Overlay for Dental Surgery". IEEE Transactions on Biomedical Engineering, vol. 61, No. 4, Apr. 2014, pp. 1295-1304.

* cited by examiner

SURGICAL NAVIGATION SYSTEM, SURGICAL NAVIGATION METHOD AND PROGRAM

This is a national phase application of PCT/JP2016/077979 filed Sep. 23, 2016, claiming priority to Japanese Patent Application No. JP2015-196791 filed Oct. 2, 2015, the contents of which are incorporated herein by reference.

TECHNICAL FIELD

The present disclosure relates to a surgical navigation system, surgical navigation method and program.

BACKGROUND

A proposed configuration of a surgical navigation system uses a retina projection-type head-mounted display (RPHMD) to project three-dimensional simulation image information of an implant on the retina of a surgeon to be overlapped on an operation site of a patient (as described in, for example, PTL 1). This system measures three-dimensional position posture of a first marker that is fixed in the mouth of the patient and three-dimensional position posture of a second marker that is fixed in the RPHMD, converts the three-dimensional simulation image information of the implant from a three-dimensional coordinates system into a surgeon field-of-view coordinates system by using the three-dimensional position postures of the first marker and of the second marker, three-dimensional position posture between the implant and the first marker, and position of the second marker, and uses the RPHMD to project the converted three-dimensional simulation image information on the retina of the surgeon to be overlapped on the operation site of the patient.

Another proposed configuration of the surgical navigation system generates a three-dimensional image for surgical navigation by using a photographed three-dimensional image that is taken by a binocular camera that tracks a patient and a surgical instrument, and overlaps the generated three-dimensional image on an operation site of the patient (as described in, for example, NPL 1). This system generates a three-dimensional image for surgical navigation by tracking of the patient and three-dimensional contour matching without requiring markers, and displays the generated three-dimensional image on a three-dimensional display to be overlapped with the operation site of the patient via a half mirror.

CITATION LIST

Patent Literature

PTL 1: JP 2010-259497A

Non-Patent Literature

NPL 1: J. Wang, H. Suenaga, K. Hoshi, L. Yang, E. Kobayashi, I. Sakuma and H. Liao, "Augmented Reality Navigation With Automatic Marker-Free Image Registration Using 3-D Image Overlay for Dental Surgery", IEEE Trans. Biomed. Eng., Vol. 61, No. 4, 1295-1304, 2014

SUMMARY

The former system needs to fix the marker in the mouth. This marker is likely to impose a burden on the patient or interfere with an operation. The latter system requires the binocular camera. In the actual state, an operating room is generally equipped with not a binocular camera but a monocular camera. Navigation of surgical information in real time accordingly needs to newly introduce the above system using the binocular camera.

A surgical navigation system, a surgical navigation method and a program of the present disclosure mainly aim to provide surgical navigation using a monocular camera without using a marker.

In order to achieve the above primary object, a surgical navigation system, surgical navigation method and program of the present disclosure employs the following configuration.

The present disclosure is directed to a surgical navigation system that provides navigation of surgical information including an operation site. The surgical navigation system includes a storage unit configured to store clustering information obtained by hierarchically clustering multiple sets of viewpoints relative to a first part including an alignment portion in a patient or in a three-dimensional model of the patient and viewpoint-corresponding images that are images when the first part is viewed from the respective viewpoints, according to a predetermined rule, such that a higher hierarchical level has a less number of the viewpoints and a lower resolution of the viewpoint-corresponding images, a monocular camera configured to photograph a second part including the alignment portion of the patient, a comparative image creator configured to convert a resolution of a photographed image that is taken by the monocular camera into a resolution in each hierarchical level of the clustering information and create a plurality of comparative images, a viewpoint searcher configured to search for a viewpoint from a first hierarchy of a highest hierarchical level to a final hierarchy of a lower hierarchical level than the first hierarchy in the clustering information, such as to search for a viewpoint having the viewpoint-corresponding image similar to the comparative image in the first hierarchy and search for a viewpoint having the viewpoint-corresponding image similar to the comparative image among viewpoints belonging to clusters that are connected with viewpoints searched for in an immediately preceding hierarchy in each hierarchy other than the first hierarchy, and an output unit configured to set a representative viewpoint based on a viewpoint that is searched for in the final hierarchy, restore position and posture of the alignment portion of the second part relative to the monocular camera as position and posture of the alignment portion of the first part relative to the representative viewpoint, generate a navigation image based on position and posture of the surgical information relative to the alignment portion of the first part after the restoration, and output the navigation image.

The surgical navigation system of this aspect stores, into the storage unit, the clustering information obtained by hierarchically clustering the multiple sets of the viewpoints relative to the first part including the alignment portion in the patient or in the three-dimensional model of the patient and the viewpoint-corresponding images that are images when the first part is viewed from the respective viewpoints, according to the predetermined rule, such that the higher hierarchical level has the less number of the viewpoints and the lower resolution of the viewpoint-corresponding images. At the time of a surgery, the surgical navigation system first takes a photographed image of the second part including the alignment portion of the patient by the monocular camera, converts the resolution of the photographed image into the resolution in each hierarchical level of the clustering information, and creates the plurality of comparative images. The surgical navigation system subsequently searches for viewpoints from the first hierarchy of the highest hierarchical level to the final hierarchy of the lower hierarchical level than the first hierarchy in the clustering information, such as to search for any viewpoint having the viewpoint-corresponding image similar to the comparative image in the first hierarchy and search for any viewpoint having the viewpoint-corresponding image similar to the comparative image among the viewpoints belonging to the clusters that are connected with the viewpoints searched for in the immediately preceding hierarchy in each hierarchy other than the first hierarchy. The surgical navigation system then sets the representative viewpoint based on the viewpoint that is searched for in the final hierarchy, restores the position and posture of the alignment portion of the second part relative to the monocular camera as the position and posture of the alignment portion of the first part relative to the representative viewpoint, generates the navigation image based on the position and posture of the surgical information relative to the alignment portion of the first part after the restoration, and outputs the navigation image. The method of this aspect allows for surgical navigation using the monocular camera without using a marker. The configuration of this aspect searches for any viewpoint having the viewpoint-corresponding image similar to the comparative image sequentially from the hierarchy having the less number of viewpoints and the lower resolution of viewpoint-corresponding images and also searches for any viewpoint having the viewpoint-corresponding image similar to the comparative image among only the viewpoints belonging to clusters that are connected with viewpoints searched for in an immediately preceding hierarchy in each of the hierarchies other than the first hierarchy. This configuration shortens the time period required from imaging with the monocular camera to searching for a viewpoint in the final hierarchy.

A technique employed to output the navigation image may be, for example, a method that projects (overlaps) the navigation image on an operation site of the patient, a method that overlaps the navigation image on a photographed image taken by the monocular camera and displays the overlapped image on a display, or a method that projects the navigation image, for example, on an eyepiece lens of a surgical microscope or on a display of a transmissive head-mounted display, to be overlapped on an operation site of the patient.

In the surgical navigation system of this aspect, the clustering information may include a hierarchical aspect graph obtained by hierarchically clustering the multiple sets according to similarity of the viewpoint-corresponding images as the predetermined rule. In the system of this aspect, the clustering information is provided as information obtained by hierarchically clustering the viewpoints according to the similarity of the viewpoint-corresponding images. Accordingly, each cluster is specified as a set of viewpoints having the viewpoint-corresponding images of the high similarity. As a result, in the process of searching for any viewpoint having the viewpoint-corresponding image similar to the comparative image in each of the hierarchies from the first hierarchy to the final hierarchy, this configuration suppresses any viewpoint corresponding to the viewpoint-corresponding image having the relatively high similarity to the comparative image from being excluded from a determination subject (from not belonging to a cluster that is connected with a viewpoint searched for in an immediately preceding hierarchy) and thereby enhances the searching accuracy of viewpoints.

In the surgical navigation system of another aspect, the clustering information may include information obtained by hierarchically clustering the multiple sets, such that a resolution of the viewpoint-corresponding image is lowered by a fixed ratio in a higher hierarchical level. The fixed ratio may be, for example, one fourth, one ninth, or one sixteenth.

In the surgical navigation system of still another aspect, the viewpoint searcher may determine whether the viewpoint-corresponding image is similar to the comparative image by comparing a predetermined region including the alignment portion in the viewpoint-corresponding image with the predetermined region in the comparative image. This configuration enables the determination of whether the viewpoint-corresponding image is similar to the comparative image to be made in a shorter time period.

In the surgical navigation system of still another aspect, the viewpoint searcher may align the viewpoint-corresponding image with the comparative image by performing at least one correction process out of rotation, parallel translation and a change in magnification of the viewpoint-corresponding image and subsequently determine whether the viewpoint-corresponding image is similar to the comparative image, and the output unit may restore the position and posture of the alignment portion of the first part relative to the representative viewpoint according to the correction process performed for a viewpoint-corresponding image corresponding to a final searched viewpoint that is a viewpoint searched for in the final hierarchy. This configuration enables the position and posture of the alignment portion of the first part relative to the representative viewpoint to be restored more appropriately.

In the surgical navigation system of still another aspect, the alignment portion may include teeth. This is especially effective for oral surgery and the like.

The present disclosure is also directed to a surgical navigation method that provides navigation of surgical information including an operation site by using clustering information obtained by hierarchically clustering multiple sets of viewpoints relative to a first part including an alignment portion in a patient or in a three-dimensional model of the patient and viewpoint-corresponding images that are images when the first part is viewed from the respective viewpoints, according to a predetermined rule, such that a higher hierarchical level has a less number of the viewpoints and a lower resolution of the viewpoint-corresponding images, and a photographed image of a second part including the alignment portion of the patient that is taken by a monocular camera. The surgical navigation method includes;

(a) a step of converting a resolution of a photographed image that is taken by the monocular camera into a resolution in each hierarchical level of the clustering information and creating a plurality of comparative images;

(b) a step of searching for a viewpoint from a first hierarchy of a highest hierarchical level to a final hierarchy of a lower hierarchical level than the first hierarchy in the clustering information, such as to search for a viewpoint having the viewpoint-corresponding image similar to the comparative image in the first hierarchy and search for a viewpoint having the viewpoint-corresponding image similar to the comparative image among viewpoints belonging to clusters that are connected with viewpoints searched for in an immediately preceding hierarchy in each hierarchy other than the first hierarchy; and (c) a step of setting a representative viewpoint based on a viewpoint that is searched for in the final hierarchy, restoring position and posture of the alignment portion of the second part relative to the monocular camera as position and posture of the alignment portion of the first part relative to the representative viewpoint, generating a navigation image based on position and posture of the surgical information relative to the alignment portion of the first part after the restoration, and outputting the navigation image.

The surgical navigation method of this aspect provides the clustering information obtained by hierarchically clustering the multiple sets of the viewpoints relative to the first part including the alignment portion in the patient or in the three-dimensional model of the patient and the viewpoint-corresponding images that are images when the first part is viewed from the respective viewpoints, according to the predetermined rule, such that the higher hierarchical level has the less number of the viewpoints and the lower resolution of the viewpoint-corresponding images. At the time of a surgery, the surgical navigation method first converts the resolution of a photographed image of the second part including the alignment portion of the patient, which is taken by the monocular camera, into the resolution in each hierarchical level of the clustering information and creates the plurality of comparative images. The surgical navigation method subsequently searches for viewpoints from the first hierarchy of the highest hierarchical level to the final hierarchy of the lower hierarchical level than the first hierarchy in the clustering information, such as to search for any viewpoint having the viewpoint-corresponding image similar to the comparative image in the first hierarchy and search for any viewpoint having the viewpoint-corresponding image similar to the comparative image among the viewpoints belonging to the clusters that are connected with the viewpoints searched for in the immediately preceding hierarchy in each hierarchy other than the first hierarchy. The surgical navigation method then sets the representative viewpoint based on the viewpoint that is searched for in the final hierarchy, restores the position and posture of the alignment portion of the second part relative to the monocular camera as the position and posture of the alignment portion of the first part relative to the representative viewpoint, generates the navigation image based on the position and posture of the surgical information relative to the alignment portion of the first part after the restoration, and outputs the navigation image. The method of this aspect allows for surgical navigation using the monocular camera without using a marker. The method of this aspect searches for any viewpoint having the viewpoint-corresponding image similar to the comparative image sequentially from the hierarchy having the less number of viewpoints and the lower resolution of viewpoint-corresponding images and also searches for any viewpoint having the viewpoint-corresponding image similar to the comparative image among only the viewpoints belonging to clusters that are connected with viewpoints searched for in an immediately preceding hierarchy in each of the hierarchies other than the first hierarchy. This configuration shortens the time period required from imaging with the monocular camera to searching for a viewpoint in the final hierarchy.

Another aspect of the present disclosure is a program that causes the computer to perform the respective steps of the surgical navigation method described above. This program may be recorded in a computer readable recording medium (for example, SSD, hard disk, ROM, FD, CD or DVD) or may be delivered from one computer to another computer via a transmission medium (communication network such as the Internet or a LAN). Execution of this program by the computer implements the respective steps of the surgical navigation method described above. This program accordingly has similar functions and advantageous effects to those of the surgical navigation method.

DESCRIPTION OF EMBODIMENTS

The following describes some aspects of the disclosure with reference to embodiments.

Figure 1:
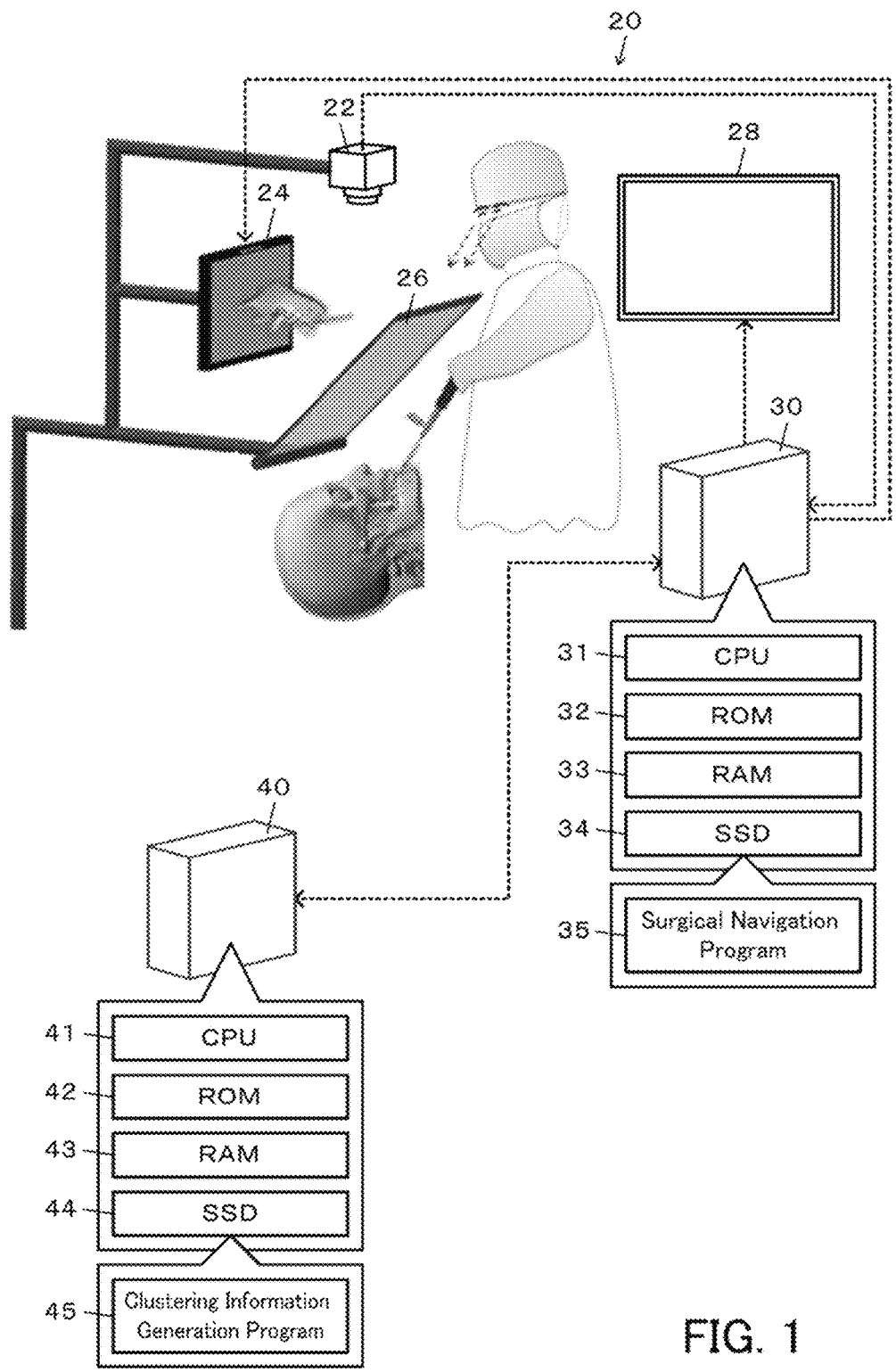
FIG. 1 is a configuration diagram illustrating the schematic configuration of a surgical navigation system 20 according to one embodiment of the present disclosure.

FIG. 1 is a configuration diagram illustrating the schematic configuration of a surgical navigation system 20 according to one embodiment of the present disclosure. As illustrated, the surgical navigation system 20 of the embodiment includes a monocular camera 22 configured to take an image of a patient, a display 24 configured to project the image on an operation site of the patient via a half mirror 26, a display 28 configured to display the image, and computers 30 and 40 as arithmetic processing units. The monocular camera 22, the display 24, the half mirror 26 and the computer 30 are placed in an operating room, and the computer 40 is placed in, for example, a location where a simulation is performed prior to a surgery. According to the embodiment, this surgical navigation system 20 is used for an oral surgery involved in, for example, the mouth, the jaw and the face.

The computer 30 is configured by installing a surgical navigation program 35 as application software in a general-purpose computer. This computer 30 includes, for example, a CPU 31, a ROM 32, a RAM 33, an SSD 34, a graphic processing unit (GPU), a system bus, input/output ports and a communication port. The surgical navigation program 35 is stored in the SSD 34. The computer 30 is connected with the monocular camera 22, the displays 24 and 28, a keyboard, a mouse and the like and allows for communication with the computer 40.

The computer 40 is configured by installing a clustering information generation program 45 as application software in a general-purpose computer. This computer 40 includes, for example, a CPU 41, a ROM 42, a RAM 43, an SSD 44, a graphic processing unit (GPU), a system bus, input/output ports and a communication port. The clustering information generation program 45 is stored in the SSD 44. The computer 40 is connected with a display, a keyboard, a mouse and the like and allows for communication with the computer 30.

The following describes operations of the surgical navigation system 20 of the embodiment and more specifically describes the processing of the clustering information generation program 45 by the computer 40 and the processing of the surgical navigation program 35 by the computer 30. Basically, a user such as a surgeon gives an instruction prior to a surgery to execute the clustering information generation program 45. The user gives an instruction at the time of a surgery (immediately before a start of a surgery) to execute the surgical navigation program 35. These are sequentially described below.

Figure 2:
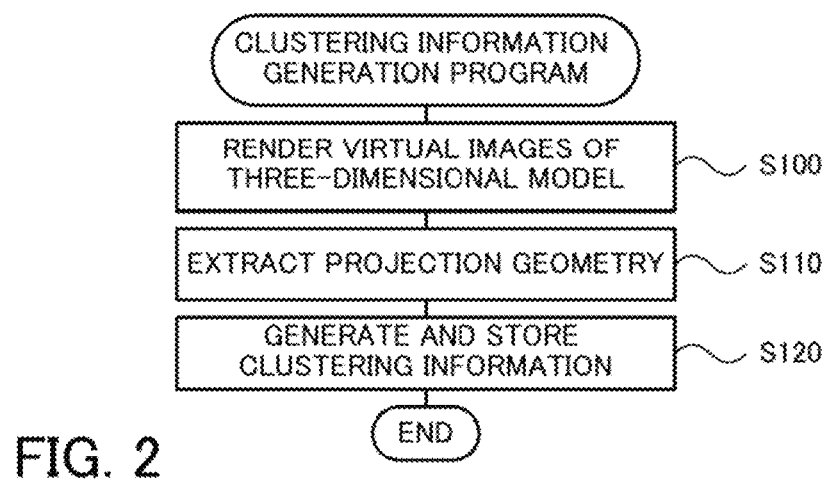
FIG. 2 is a flowchart showing one example of a clustering information generation program 45.

FIG. 2 is a flowchart showing one example of the clustering information generation program 45. The clustering information generation program 45 is read out from the SSD 44 and is written into the RAM 43 to be executed by the CPU 41, in response to the user's execution instruction. According to the embodiment, prior to execution of this program, the surgeon or the like creates a three-dimensional model of a patient's head including teeth as an alignment portion using the patient's CT (Computed Tomography) data or the like, adds surgical information to the three-dimensional model, and performs a simulation (creation of a surgical plan) or the like prior to a surgery. The alignment portion used here is preferably maxillary teeth in the case of a craniofacial surgery such as a maxillary surgery and is preferably mandibular teeth in the case of a mandibular surgery. The surgical information may be, for example, a punching position, a cutting position, a cutting surface, an excision position, a transplanting position, and positions of blood vessels and nerves, in addition to the three-dimensional image such as CT.

Figure 3:
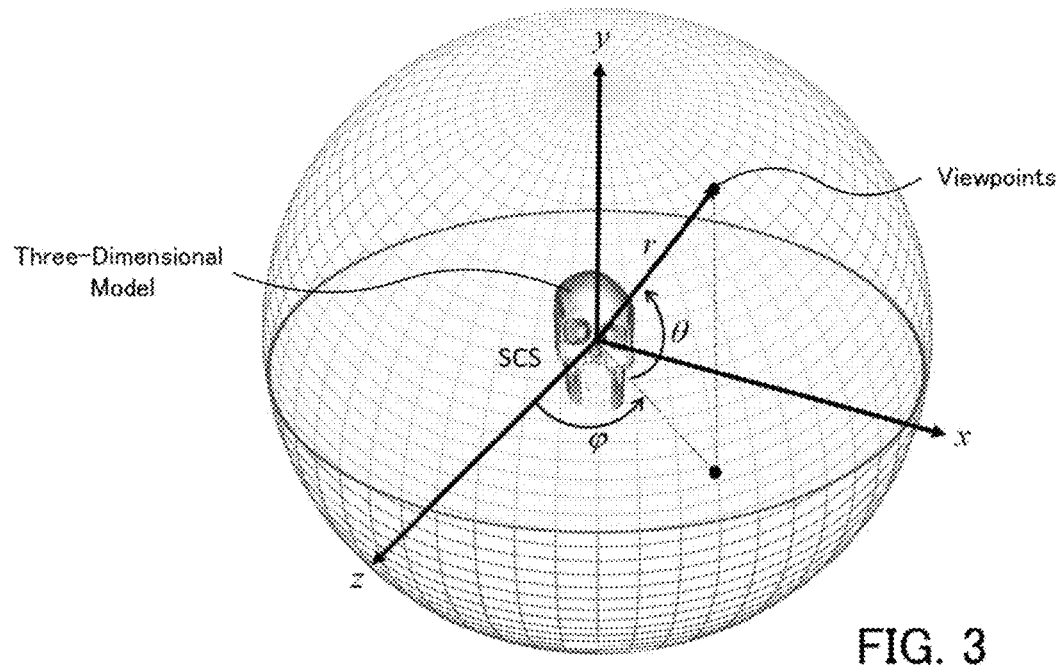
FIG. 3 is a diagram illustrating a process of placing a three-dimensional model at the center and setting viewpoints.
Figure 4:
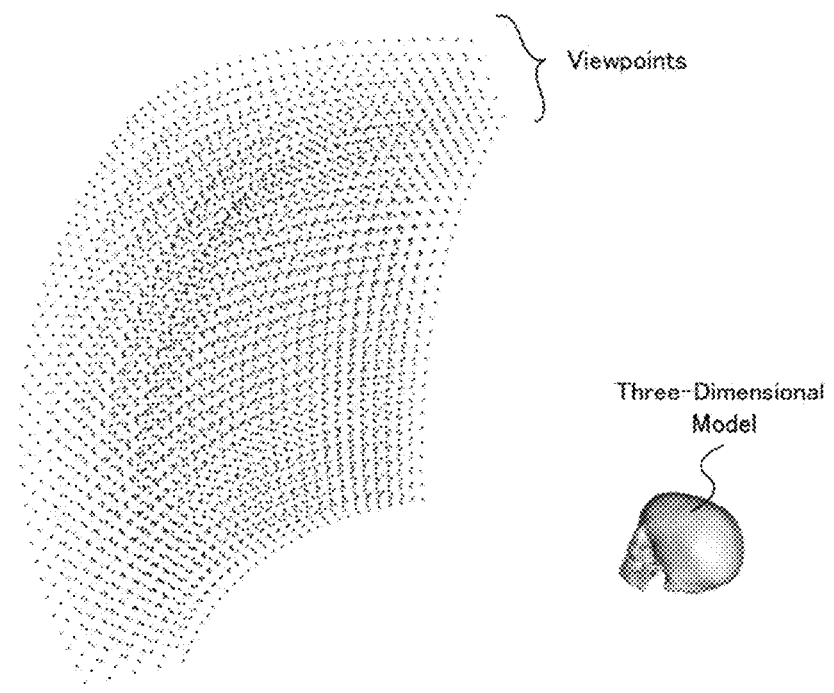
FIG. 4 is a diagram illustrating the positions of the respective viewpoints relative to the three-dimensional model.
Figure 5:
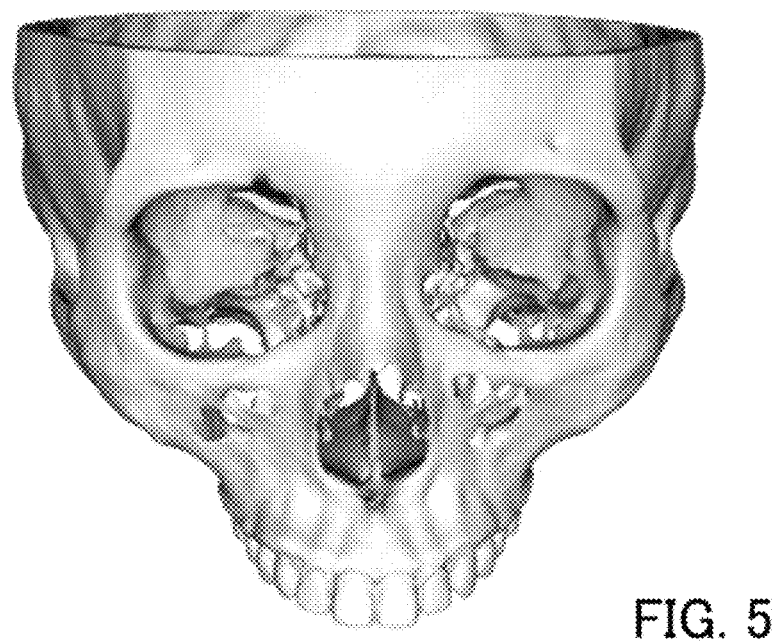
FIG. 5 is a diagram illustrating a virtual image of the three-dimensional model from a given viewpoint.

When the clustering information generation program 45 is triggered, the CPU 41 first sets multiple viewpoints in a three-dimensional model of a head including teeth, renders virtual images by CG (computer graphics) when the three-dimensional model is viewed from the respective viewpoints, and relates the respective viewpoints to the respective virtual images (step S100). FIG. 3 is a diagram illustrating a process of placing a three-dimensional model at the center (center of an orthogonal coordinates system specified by three axes, i.e., an x axis, a y axis and a z axis) and setting viewpoints. FIG. 4 is a diagram illustrating the positions of the respective viewpoints relative to the three-dimensional model. FIG. 5 is a diagram illustrating a virtual image of the three-dimensional model from a given viewpoint. FIGS. 3 to 5 illustrate a case that does not use a patient's three-dimensional model but uses an artificial three-dimensional model. In FIG. 3, "SCS" represents Spherical Coordinates System; "r" denotes a distance from the center to a viewpoint; "φ" denotes an angle of the position of the viewpoint projected on a zx plane, to the z axis (where the x-axis side is positive); and θ denotes an angle of the viewpoint to the zx plane (where the y-axis side is positive). The ranges of each viewpoint may be, for example, 1.2 m≤r≤1.4 m, −30°≤φ≤30° and −30°≤θ≤30°.

Figure 6:
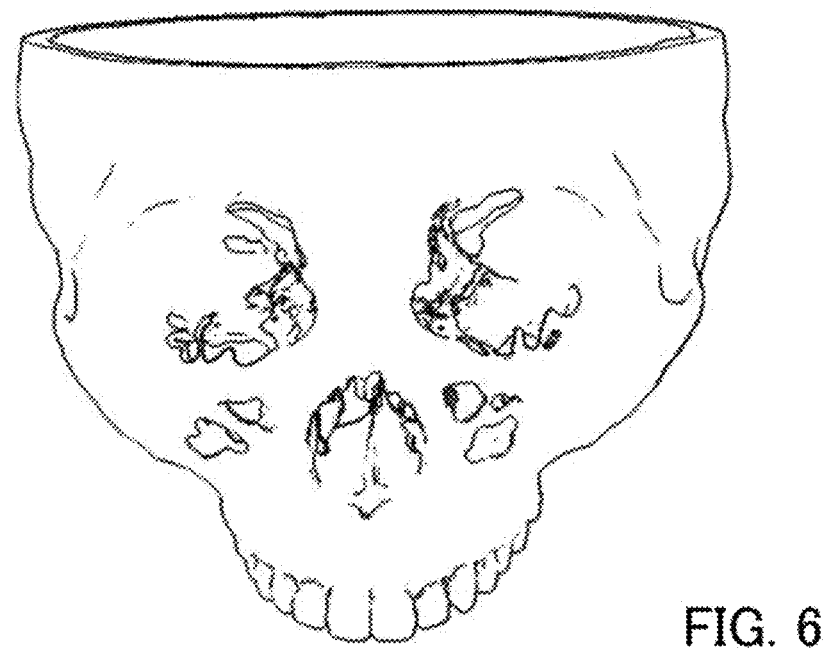
FIG. 6 is a diagram illustrating a projection image created from the virtual image of FIG. 5.

The CPU 41 subsequently extracts a projection geometry of the three-dimensional model from each virtual image to create a two-dimensional projection image and relates the respective viewpoints to the respective projection images (step S110). FIG. 6 is a diagram illustrating a projection image created from the virtual image of FIG. 5. This process reduces the data volume of the image.

The CPU 41 then generates clustering information and stores the generated clustering information into the SSD 44 (step S120) and terminates this routine. According to the embodiment, a hierarchical aspect graph is generated as the clustering information. The aspect herein means a cluster including at least one viewpoint having a similar projection image. The hierarchical aspect graph is generated by creating multiple sets of viewpoints and projection images in an ascending direction of hierarchy such that the higher hierarchical level has the less number of viewpoints and the lower resolution of projection images that is lowered by a fixed ratio, and hierarchically clustering the viewpoints according to the similarity of the projection images. The determination of whether two projection images are similar to each other may be made by, for example, determining whether the number of pixels having a difference in a pixel value (for example, luminance) between two projection images that is equal to or less than a predetermined difference (hereinafter referred to as "number of similar pixels") is equal to or greater than a predetermined number of pixels. The fixed ratio may be, for example, one fourth, one ninth or one sixteenth. Lowering of the resolution of the projection image (down sampling) may be implemented by, for example, a nearest neighbor method, a bilinear method or a bicubic method.

Figure 7:
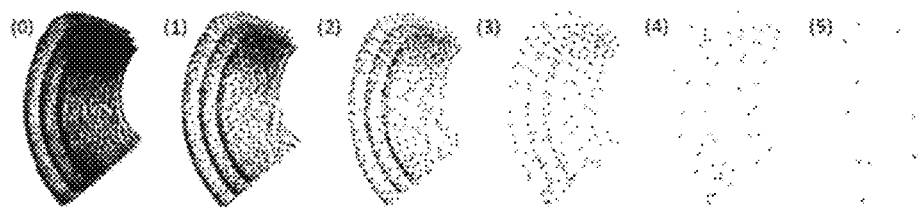
FIG. 7 is a diagram illustrating viewpoints in respective hierarchical levels.
Figure 8:
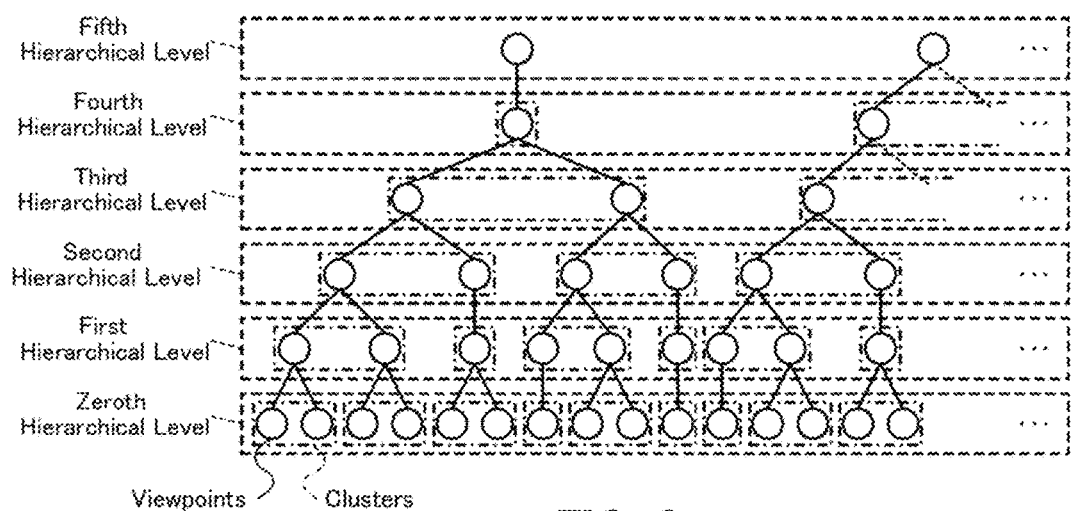
FIG. 8 is a diagram illustrating part of a hierarchical aspect graph.

FIG. 7 is a diagram illustrating viewpoints in respective hierarchical levels. FIG. 8 is a diagram illustrating part of a hierarchical aspect graph. Open circles in FIG. 8 represent viewpoints. As shown in FIGS. 7 and 8, a hierarchical aspect graph of six hierarchical levels from a zeroth hierarchical level to a fifth hierarchical level is generated according to the embodiment. In the zeroth hierarchical level, viewpoints (and projection images corresponding to the respective viewpoints) set by the processing of step S100 are classified into multiple clusters according to the similarity of the projection images (where each cluster is comprised of viewpoints having similar projection images). In each of the first to the fourth hierarchical levels, viewpoints created from clusters of an immediate lower hierarchical level (and projection images) are classified into multiple clusters according to the similarity of the projection images. Viewpoints and projection images in an immediate higher hierarchical level are then created from viewpoints (and projection images) of each cluster, and the viewpoints and the projection images in each hierarchical level are related to those in a different hierarchical level. With regard to a cluster which one viewpoint belongs to in a present hierarchical level, the one viewpoint and a projection image that corresponds to the one viewpoint and has a lowered resolution are created as a viewpoint and a projection image in an immediate higher hierarchical level. With regard to a cluster which a plurality of viewpoints belong to, a new viewpoint having average coordinates of the plurality of viewpoints and a projection image that corresponds to the new viewpoint and has a lowered resolution are created as a viewpoint and a projection image in an immediate higher hierarchical level. The resolutions in the respective hierarchical levels may be specified as follows: for example, 2048×2048 as the resolution of the zeroth hierarchical level, 1024×1024 as the resolution of the first hierarchical level, and 64×64 as the resolution of the fifth hierarchical level.

Figure 9:
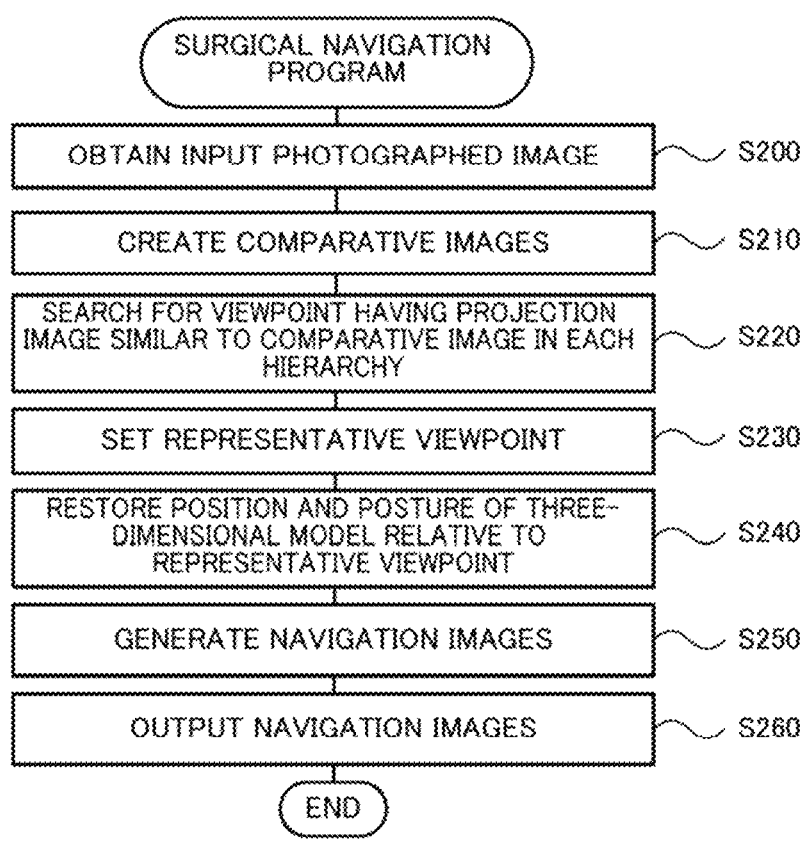
FIG. 9 is a flowchart showing one example of a surgical navigation program 35.

The following describes the processing of the surgical navigation program 35 by the computer 30. FIG. 9 is a flowchart showing one example of the surgical navigation program 35. The surgical navigation program 35 is readout from the SSD 34 and is written into the RAM 33 by the CPU 31, in response to the user's execution instruction. The surgical navigation program 35 is then executed, every time a photographed image is received from the monocular camera 22. According to the embodiment, it is assumed that the surgeon or the like copies or moves a file of the clustering information stored in the SSD 44 of the computer 40 to the SSD 34 of the computer 30, prior to execution of this program. It is also assumed that an image of the periphery of teeth is taken by the monocular camera 22 as the alignment portion of the patient.

When the surgical navigation program 35 is triggered, the CPU 31 first inputs two-dimensional photographed image taken by the monocular camera 22 (step S200) and converts the resolution of the photographed image into a resolution of images in each hierarchical level of the hierarchical aspect graph and creates a plurality of comparative images (step S210). According to the embodiment, the hierarchical aspect graph of the six hierarchical levels from the zeroth hierarchical level to the fifth hierarchical level is created, so that comparative images of the respective resolutions in the zeroth hierarchical level to the fifth hierarchical level are created.

Figure 10:
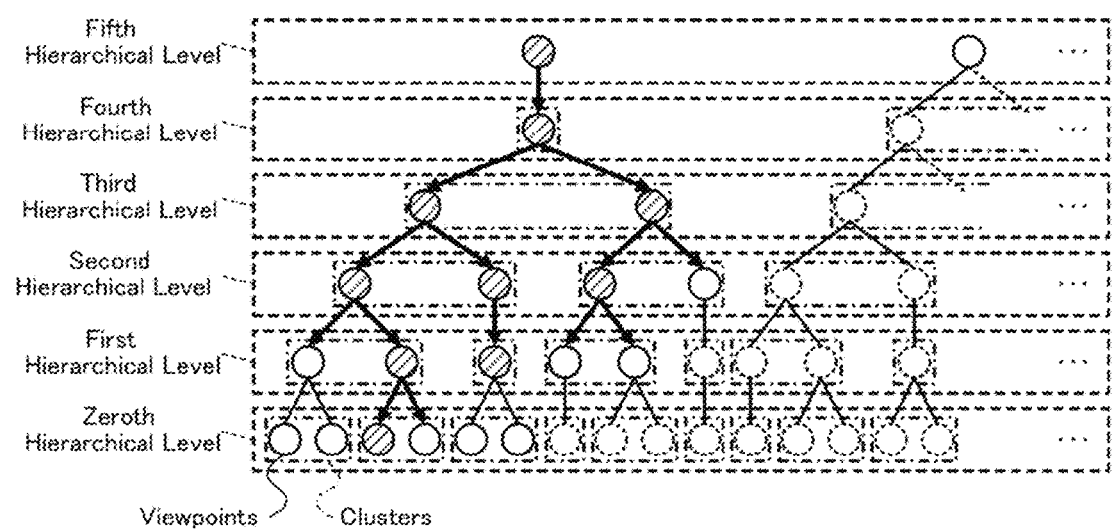
FIG. 10 is a diagram illustrating searching for any viewpoint having a projection image similar to a comparative image in each hierarchy.

Subsequently the CPU 31 searches for any viewpoint having a projection image similar to the comparative image sequentially from a first hierarchy of the highest hierarchical level to a final hierarchy of the lowest hierarchical level in the clustering information (hierarchical aspect graph) (step S220). FIG. 10 is a diagram illustrating searching for any viewpoint having a projection image similar to a comparative image in each hierarchy. In FIG. 10, solid-line circles represent viewpoints of determination subjects (viewpoints subjected to determination of whether a projection image is similar to a comparative image), and dotted-line circles represent viewpoints of non-determination subjects. Among the solid-line circles, hatched circles represent viewpoints that are searched for, and non-hatched circles represent viewpoints that are not searched for. A base end of each thick arrow indicates a viewpoint searched for in an upper hierarchy, and a leading end of the thick arrow indicates a viewpoint belonging to a cluster that is connected with the viewpoint searched for in the upper hierarchy. In the first hierarchy (the fifth hierarchical level), all the viewpoints belonging to the first hierarchy are specified as viewpoints of determination subjects, and any viewpoint having a projection image similar to a comparative image is searched for, among these viewpoints of determination subjects. In each of hierarchies other than the first hierarchy (the fourth hierarchical level to the zeroth hierarchical level), viewpoints belonging to clusters that are connected with viewpoints searched for in an immediately preceding hierarchy are specified as viewpoints of determination subjects, and any viewpoint having a projection image similar to a comparative image is searched for, among these viewpoints of determination subjects. Employing the strategies that (1) only viewpoints belonging to clusters that are connected with viewpoints searched for in an immediately preceding hierarchy are specified as viewpoints of determination subjects in each of hierarchies other than the first hierarchy and that (2) the higher hierarchical level has the lower resolution of the projection image and the comparative image shortens the time period required from imaging with the monocular camera 22 to searching for a viewpoint in the final hierarchy (the zeroth hierarchical level). Each cluster is specified as a set of viewpoints having projection images of the high similarity. In the process of searching for any viewpoint having a projection image similar to a comparative image in each of hierarchies from the first hierarchy to the final hierarchy, this configuration suppresses any viewpoint corresponding to a projection image having the relatively high similarity to the comparative image from being excluded from the determination subject (from not belonging to a cluster that is connected with a viewpoint searched for in the immediately preceding hierarchy) and thereby enhances the searching accuracy of viewpoints.

Figure 11:
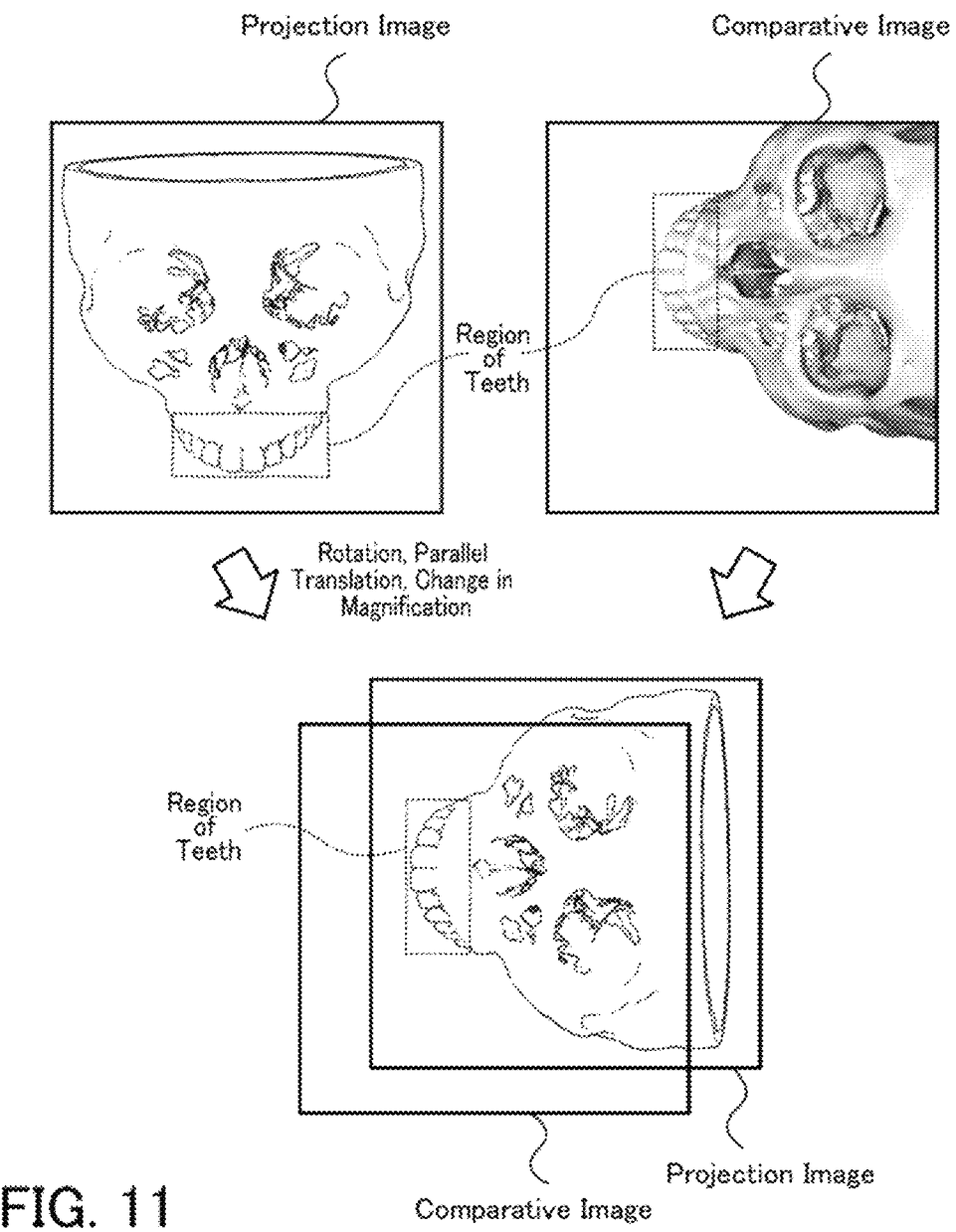
FIG. 11 is a diagram illustrating a procedure of determining whether a projection image is similar to a comparative image.

The determination of whether a projection image is similar to a comparative image is made by a procedure described below. FIG. 11 is a diagram illustrating a procedure of determining whether a projection image is similar to a comparative image. FIG. 11 does not use images of a patient and its three-dimensional model but uses images of an artificial model and its three-dimensional model, like FIGS. 3 to 5. The procedure first selects a region of teeth from the projection image and from the comparative image. The region of teeth may be selected by, for example, comparing pixel values (for example, luminance values) with a reference value. The region of teeth is selected as a rectangular region. The procedure subsequently aligns the projection image with the comparative image, such that the region of teeth in the projection image matches the region of teeth in the comparative image to some extent. The alignment of the projection image may be performed by, for example, causing the projection image to be subjected to at least one of rotation about an axis that passes through the center of the projection image, parallel translation and a change in magnification, such that, for example, the number of pixels included in the rectangular region, the longitudinal direction and the short direction of the rectangular region, and the center of the rectangular region in the projection image are approximately identical with those in the comparative image. In such alignment, γ denotes the rotational angle, tx and tx denote moving distances (numbers of pixels) in a horizontal direction and in a vertical direction, and σ denotes the magnification. When the region of teeth in the projection image prior to the alignment matches the region of teeth in the comparative example to some extent, there is no need for this alignment. In this case, the rotational angle γ and the moving distances tx and ty may be set equal to 0, and the magnification σ may be set equal to 1. The procedure then compares the region of teeth in the projection image after the alignment with the region of teeth in the comparative example and determines whether the projection image is similar to the comparative image. This determination may be made by, for example, determining whether the number of pixels having similarity between the respective regions of teeth (number of pixels having a difference in pixel value that is equal to or less than a predetermined difference) is equal to or greater than a predetermined number of pixels. The configuration that compares the region of teeth in the projection image with the region of teeth in the comparative image to determine whether the projection image is similar to the comparative image shortens the time period required for searching for viewpoints in each hierarchy and thereby the time period required until completion of searching for a viewpoint in the final hierarchy (the zeroth hierarchical level), compared with a configuration that compares the entire overlapping regions of the projection image and the comparative image to determine the similarity.

The CPU 31 subsequently sets a representative viewpoint, based on a final searched viewpoint that is a viewpoint searched for in the final hierarchy (step S230), and restores the position and posture of the teeth of the patient relative to the monocular camera 22 as the position and posture of the teeth of the three-dimensional model relative to the representative viewpoint (step S240). According to the embodiment, this restoration is performed by adding surgical information to the three-dimensional model. When there is only one final searched viewpoint, the processing of steps S230 and S240 sets the final searched viewpoint as the representative viewpoint and restores the position and posture of the teeth of the three-dimensional model relative to the representative viewpoint, based on values (γ, tx, ty, σ) in comparison of a projection image corresponding to the final searched viewpoint with the comparative image. When there are a plurality of final searched viewpoints, on the other hand, the processing of steps S230 and S240 sets average coordinates of the plurality of final searched viewpoints as the representative viewpoint and restores the position and posture of the teeth of the three-dimensional model relative to the representative viewpoint, based on average values of multiple sets of values (γ, tx, ty, σ) in comparison of a plurality of projection images corresponding to the plurality of final searched viewpoints with the comparative image. With referring to FIG. 3, the restoration of the position and posture of the teeth of the three-dimensional model relative to the representative viewpoint sets a straight line connecting the center with the representative viewpoint and its extension as a predetermined axis, rotates the three-dimensional model (teeth) along with surgical information about the predetermined axis according to the rotation angle γ, moves the three-dimensional model in a direction perpendicular to the predetermined axis according to the moving distances tx and ty, and further moves the three-dimensional model in a direction of the predetermined axis according to the magnification σ. When this process is still insufficient, it is preferable to restore the position and posture of the teeth of the three-dimensional model relative to the representative viewpoint again by an additional process such as least squares method.

The CPU 31 subsequently generates two-dimensional and three-dimensional navigation images (step S250). The two-dimensional and three-dimensional images may be generated, based on the position and posture of the surgical information relative to the teeth of the three-dimensional model. The position and posture of the teeth of the three-dimensional model relative to the representative viewpoint are restored after addition of surgical information to the three-dimensional model (teeth). Accordingly, an image of the surgical information added to the three-dimensional model after the restoration viewed from the representative viewpoint is generated as the navigation image. This means that the navigation image denotes an image that sufficiently reflects the position and posture of the surgical information two-dimensionally or three-dimensionally relative to the teeth of the three-dimensional model when being viewed from the representative viewpoint.

The CPU 31 then outputs the generated navigation images (step S260) and terminates this routine. According to the embodiment, the three-dimensional navigation image is projected (overlapped) from the display 24 via the half mirror 26 on an operation site of the patient. The two-dimensional navigation image is overlapped on a photographed image taken by the monocular camera 22 and is displayed on the display 28. The position and the angle of the half mirror 26 are adjusted in advance prior to a surgery, such that an appropriate navigation image displayed on the display 24 is adequately projected on an operation site. This series of processing provides surgical navigation.

Figure 12:
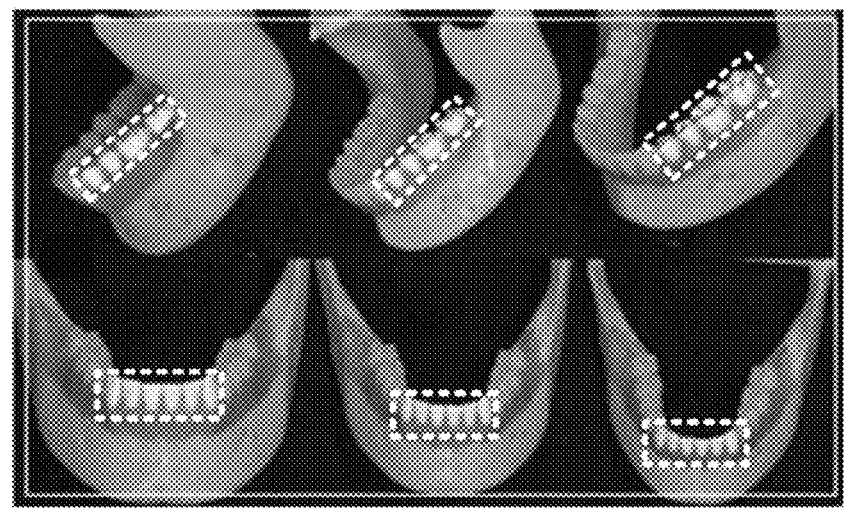
FIG. 12 is diagrams illustrating results of an experiment that generates a navigation image and overlaps the navigation image on a photographed image taken by a monocular camera 22 according to a method of the embodiment.
Figure 13:
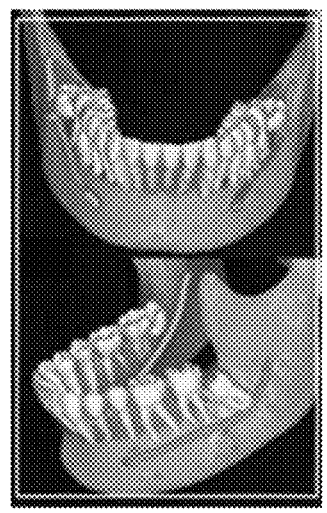
FIG. 13 is diagrams illustrating results of the experiment that generates the navigation image and overlaps the navigation image on the photographed image taken by the monocular camera 22 according to the method of the embodiment.

FIG. 12 and FIG. 13 are diagrams illustrating results of an experiment that generates a navigation image and overlaps the navigation image on a photographed image taken by the monocular camera 22 according to the method of the embodiment. This experiment did not use the patient but used an artificial model. FIG. 12 shows the results when navigation images of some parts of teeth (teeth encircled by dotted lines) are overlapped on photographed images. FIG. 13 shows the results when navigation images of all teeth and nerves are overlapped on photographed images. The upper drawings of FIG. 12 (regions of left posterior teeth) had an alignment error of approximately 0.87 mm, and the lower drawings of FIG. 12 (regions of anterior teeth) had an alignment error of approximately 0.75 mm. The allowable error is generally approximately 1 mm in the field of oral surgery. These results indicate that the navigation image is overlapped on the photographed image with high accuracy by the method of the embodiment. The time period required from imaging with the monocular camera 22 to the display of the image shown in FIG. 11 was approximately 300 msec to 400 msec. By setting the interval of imaging by the monocular camera 22 to about several hundred msec, the navigation image is expected to sufficiently follow the motion of the patient (operation site) during a surgery. Additionally, the results of FIG. 13 show that even the superficially invisible structure (for example, nerves) can be displayed as a navigation image (to allow for surgical navigation).

The surgical navigation system 20 of the embodiment described above stores, into the SSD 34, the clustering information that is obtained by hierarchically clustering multiple sets of viewpoints relative to a three-dimensional model of a patient (i.e., ahead including teeth) and projection images when the three-dimensional model is viewed from the respective viewpoints, according to the similarity of the projection images, such that the higher hierarchical level has the less number of viewpoints and the lower resolution of the projection images. At the time of a surgery, a photographed image of the periphery of teeth of the patient is taken by the monocular camera 22. The surgical navigation system 20 searches for viewpoints by using comparative images created from the photographed image, from the first hierarchy of the highest hierarchical level to the final hierarchy of the lower hierarchical level than the first hierarchy in the clustering information. In the first hierarchy, the surgical navigation system 20 searches for any viewpoint having a projection image similar to the comparative image. In each of the hierarchies other than the first hierarchy, the surgical navigation system 20 searches for any viewpoint having a projection image similar to the comparative image, among viewpoints belonging to clusters that are connected with viewpoints searched for in an immediately preceding hierarchy. The surgical navigation system 20 subsequently sets a representative viewpoint, based on a final searched viewpoint that is the viewpoint searched for in the final hierarchy. The surgical navigation system 20 then restores the position and posture of the teeth of the patient relative to the monocular camera 22 as the position and posture of the teeth of the three-dimensional model relative to the representative viewpoint, generates a navigation image based on the position and posture of the surgical information relative to the teeth of the three-dimensional model after the restoration, and outputs the navigation image. This method allows for surgical navigation using the monocular camera 22 without using any markers. This method searches for any viewpoint having a projection image similar to the comparative image sequentially from the hierarchy having the less number of viewpoints and the lower resolution of projection images and also searches for any viewpoint having a projection image similar to the comparative image among only the viewpoints belonging to clusters that are connected with viewpoints searched for in an immediately preceding hierarchy in each of the hierarchies other than the first hierarchy. This configuration shortens the time period required from imaging with the monocular camera 22 to searching for a viewpoint in the final hierarchy and thereby to output of a navigation image.

The surgical navigation system 20 of the embodiment uses the teeth as the alignment portion. The alignment portion used may, however, be a portion other than the teeth, for example, the gum or an implant mounted to the patient in a previous surgery before a present surgery (that is not an exclusive marker used only in a present surgery).

The surgical navigation system 20 of the embodiment creates multiple sets of viewpoints and projection images from a three-dimensional model of the patient and generates clustering information. A modification may create multiple sets of viewpoints and projection images from CT data of the patient or the like without creating a three-dimensional model of the patient and generate clustering information. In this modification, the surgical information may be written in the CT data or the like.

In the surgical navigation system 20 of the embodiment, the clustering information is the hierarchical aspect graph that is clustered in six hierarchical levels according to the similarity of projection images. The number of hierarchical levels is, however, not limited to six but may four, five, seven, eight or the like. The clustering information may be clustered according to a factor other than the similarity of projection images, for example, the positional relationship of viewpoints (for example, deviations of "r", "ϕ" and "θ" shown in FIG. 3) or the number of viewpoints.

The surgical navigation system 20 of the embodiment lowers the resolution of projection images by a fixed rate in the higher hierarchical level in the process of generating the clustering information. As long as the resolution of projection images is lowered in the higher hierarchical level, the lowering rate is not limited to the fixed ratio.

The surgical navigation system 20 of the embodiment searches for any viewpoint having a projection image similar to the comparative image sequentially from the first hierarchy of the highest hierarchical level to the final hierarchy of the lowest hierarchical level (from the fifth hierarchical level to the zeroth hierarchical level in FIG. 10) in the clustering information (hierarchical aspect graph). The final hierarchy may, however, be any hierarchy of the lower hierarchical level than the first hierarchy and may be any hierarchy other than the hierarchy of the lowest hierarchical level (for example, the first hierarchical level or the second hierarchical level in FIG. 10).

The surgical navigation system 20 of the embodiment determines whether a projection image is similar to the comparative image by comparing the region of teeth in the projection image with the region of teeth in the comparative image. A modification may determine whether a projection image is similar to the comparative image by comparing the entire overlapping regions of the projection image and the comparative image.

In the surgical navigation system 20 of the embodiment, a three-dimensional navigation image is projected (overlapped) from the display 24 via the half mirror 26 on an operation site of the patient. A two-dimensional navigation image is overlapped on a photographed image taken by the monocular camera 22 and is displayed on the display 28. A modification may perform only either of these processes. According to another modification, the three-dimensional or two-dimensional navigation image may be projected, for example, on an eyepiece lens of a surgical microscope or on a transmissive head-mounted display to be overlapped with an operation site of the patient. In this modification, it is preferable to mount the monocular camera in the periphery of an objective lens of the surgical microscope or in the periphery of a transmission part of the head-mounted display, such that the field of view of the monocular camera 22 approximately matches the field of view of the surgical microscope or the head-mounted display. This configuration reduces a deviation of the projection position of the navigation image from the viewpoint of the monocular camera 22. As a result, this configuration provides the surgeon with the navigation image that is overlapped with the operation site with the higher accuracy.

In the surgical navigation system 20 of the embodiment, the monocular camera 22 and the computer 30 are configured as separate bodies. According to a modification, however, these may be integrated with each other.

The surgical navigation system 20 of the embodiment is employed for an oral surgery. The subject of the surgical navigation system 20 is, however, not limited to the oral surgery but may be any other surgery.

The embodiment describes application of the present disclosure to the surgical navigation system 20. The present disclosure may, however, be implemented as a surgical navigation method that performs the respective steps of the surgical navigation program shown in FIG. 9 or as a program that causes the computer to perform the respective steps of the surgical navigation method.

The following describes the correspondence relationship between the primary elements of the above embodiment and the primary elements of the disclosure described in Summary. The SSDs 34 and 44 configured to store the clustering information (hierarchical aspect graph) according to the embodiment correspond to the "storage unit", and the monocular camera 22 corresponds to the "monocular camera". The CPU 31 of the computer 30 configured to perform the processing of step S210 in the surgical navigation program shown in FIG. 9 corresponds to the "comparative image creator". The CPU 31 of the computer 30 configured to perform the processing of step S220 in the surgical navigation program shown in FIG. 9 corresponds to the "viewpoint searcher". The CPU 31 of the computer 30 configured to perform the processing of steps S230 to S260 in the surgical navigation program shown in FIG. 9 corresponds to the "output unit".

The correspondence relationship between the primary components of the embodiment and the primary components of the disclosure, regarding which the problem is described in Summary, should not be considered to limit the components of the disclosure, regarding which the problem is described in Summary, since the embodiment is only illustrative to specifically describes the aspects of the disclosure, regarding which the problem is described in Summary. In other words, the disclosure, regarding which the problem is described in Summary, should be interpreted on the basis of the description in the Summary, and the embodiment is only a specific example of the disclosure, regarding which the problem is described in Summary.

The aspect of the disclosure is described above with reference to the embodiment. The disclosure is, however, not limited to the above embodiment but various modifications and variations may be made to the embodiment without departing from the scope of the disclosure.

INDUSTRIAL APPLICABILITY

The technique of the disclosure is preferably applicable to the field of surgical navigation system and so on.

The invention claimed is:

1. A surgical navigation system that provides navigation of surgical information including an operation site, the surgical navigation system comprising:
a memory configured to store clustering information obtained by hierarchically clustering multiple sets of viewpoints relative to a first part including an alignment portion in a patient or in a three-dimensional model of the patient and viewpoint-corresponding images that are images when the first part is viewed from the respective viewpoints, according to a predetermined rule, such that a higher hierarchical level has a less number of the viewpoints and a lower resolution of the viewpoint-corresponding images;
a monocular camera configured to photograph a second part including the alignment portion of the patient; and
a processor programmed to:
convert a resolution of a photographed image that is taken by the monocular camera into a resolution in each hierarchical level of the clustering information and create a plurality of comparative images;
search for a viewpoint from a first hierarchy of a highest hierarchical level to a final hierarchy of a lower hierarchical level than the first hierarchy in the clustering information, including searching for a viewpoint having the viewpoint-corresponding image similar to the comparative image in the first hierarchy and searching for a viewpoint having the viewpoint-corresponding image similar to the comparative image among viewpoints belonging to clusters that are connected with viewpoints searched for in an immediately preceding hierarchy in each hierarchy other than the first hierarchy; and
set a representative viewpoint based on a viewpoint that is searched for in the final hierarchy, restore position and posture of the alignment portion of the second part relative to the monocular camera as position and posture of the alignment portion of the first part relative to the representative viewpoint, generate a navigation image based on position and posture of the surgical information relative to the alignment portion of the first part after the restoration, and output the generated navigation image.

2. The surgical navigation system according to claim 1, wherein the clustering information comprises a hierarchical aspect graph obtained by hierarchically clustering the multiple sets according to similarity of the viewpoint-corresponding images as the predetermined rule.

3. The surgical navigation system according to claim 1, wherein the clustering information comprises information obtained by hierarchically clustering the multiple sets, such that a resolution of the viewpoint-corresponding image is lowered by a fixed ratio in a higher hierarchical level.

4. The surgical navigation system according to claim 1, wherein the processor determines whether the viewpoint-corresponding image is similar to the comparative image by comparing a predetermined region including the alignment portion in the viewpoint-corresponding image with the predetermined region in the comparative image.

5. The surgical navigation system according to claim 1, wherein
the processor aligns the viewpoint-corresponding image with the comparative image by performing at least one correction process out of rotation, parallel translation and a change in magnification of the viewpoint-corresponding image and subsequently determines whether the viewpoint-corresponding image is similar to the comparative image, and
the processor restores the position and posture of the alignment portion of the first part relative to the representative viewpoint according to the correction process performed for a viewpoint-corresponding image corresponding to a final searched viewpoint that is a viewpoint searched for in the final hierarchy.

6. The surgical navigation system according to claim 1, wherein the alignment portion comprises teeth.

7. A surgical navigation method that provides navigation of surgical information including an operation site by using:
clustering information obtained by hierarchically clustering multiple sets of viewpoints relative to a first part including an alignment portion in a patient or in a three-dimensional model of the patient and viewpoint-corresponding images that are images when the first part is viewed from the respective viewpoints, according to a predetermined rule, such that a higher hierarchical level has a less number of the viewpoints and a lower resolution of the viewpoint-corresponding images; and
a photographed image of a second part including the alignment portion of the patient that is taken by a monocular camera,
the surgical navigation method comprising:
converting a resolution of a photographed image that is taken by the monocular camera into a resolution in each hierarchical level of the clustering information and creating a plurality of comparative images;
searching for a viewpoint from a first hierarchy of a highest hierarchical level to a final hierarchy of a lower hierarchical level than the first hierarchy in the clustering information, including searching for a viewpoint having the viewpoint-corresponding image similar to the comparative image in the first hierarchy and searching for a viewpoint having the viewpoint-corresponding image similar to the comparative image among viewpoints belonging to clusters that are connected with viewpoints searched for in an immediately preceding hierarchy in each hierarchy other than the first hierarchy; and
setting a representative viewpoint based on a viewpoint that is searched for in the final hierarchy, restoring position and posture of the alignment portion of the second part relative to the monocular camera as position and posture of the alignment portion of the first part relative to the representative viewpoint, generating a navigation image based on position and posture of the surgical information relative to the alignment portion of the first part after the restoration, and outputting the generated navigation image.

8. A non-transitory computer readable medium storing a program for a surgical navigation system having: (i) a memory configured to store clustering information obtained by hierarchically clustering multiple sets of viewpoints relative to a first part including an alignment portion in a patient or in a three-dimensional model of the patient and viewpoint-corresponding images that are images when the first part is viewed from the respective viewpoints, according to a predetermined rule, such that a higher hierarchical level has a less number of the viewpoints and a lower resolution of the viewpoint-corresponding images, and (ii) a monocular camera configured to photograph a second part including the alignment portion of the patient, the program causing a computer to perform steps comprising:

converting a resolution of a photographed image that is taken by the monocular camera into a resolution in each hierarchical level of the clustering information and creating a plurality of comparative images;

searching for a viewpoint from a first hierarchy of a highest hierarchical level to a final hierarchy of a lower hierarchical level than the first hierarchy in the clustering information, including searching for a viewpoint having the viewpoint-corresponding image similar to the comparative image in the first hierarchy and searching for a viewpoint having the viewpoint-corresponding image similar to the comparative image among viewpoints belonging to clusters that are connected with viewpoints searched for in an immediately preceding hierarchy in each hierarchy other than the first hierarchy; and setting a representative viewpoint based on a viewpoint that is searched for in the final hierarchy, restoring position and posture of the alignment portion of the second part relative to the monocular camera as position and posture of the alignment portion of the first part relative to the representative viewpoint, generating a navigation image based on position and posture of the surgical information relative to the alignment portion of the first part after the restoration, and outputting the generated navigation image.

* * * * *